US009250256B2

(12) United States Patent
Lukhaub et al.

(10) Patent No.: US 9,250,256 B2
(45) Date of Patent: Feb. 2, 2016

(54) CUVETTE HANDLING DEVICE (71) Applicant: STRATEC Biomedical AG, Birkenfeld (DE)

(72) Inventors: Waldemar Lukhaub, Birkenfeld (DE); Alexander Schramm, Birkenfeld (DE); Martin Trump, Birkenfeld (DE)

(73) Assignee: STRATEC Biomedical AG, Birkenfeld (DE)

( * ) Notice: Subject to any disclaimer, the term of this patent is extended or adjusted under 35 U.S.C. 154(b) by 0 days.

(21) Appl. No.: 14/247,622

(22) Filed: Apr. 8, 2014

(65) Prior Publication Data
US 2014/0319163 A1 Oct. 30, 2014

(30) Foreign Application Priority Data

Apr. 30, 2013 (GB) .................................. 1307768.0

(51) Int. Cl.
G07F 11/16 (2006.01)
B65H 3/28 (2006.01)
G01N 35/02 (2006.01)
G01N 35/04 (2006.01)
B65G 59/10 (2006.01)

(52) U.S. Cl.
CPC ............ *G01N 35/025* (2013.01); *B65G 59/105* (2013.01); *G01N 35/04* (2013.01); *G01N 2035/0401* (2013.01)

(58) Field of Classification Search
CPC .................................................. G01N 35/025
USPC ......... 221/1, 220, 116, 223, 6, 297, 221, 289, 221/295, 303, 268; 422/63
See application file for complete search history.

(56) References Cited

U.S. PATENT DOCUMENTS

| 2,261,880 | A | * | 11/1941 | Hope | ...................... A47F 1/106 |
| | | | | | 221/198 |
| 2,834,511 | A | * | 5/1958 | Booth | ...................... G07F 13/10 |
| | | | | | 221/116 |
| 3,265,243 | A | * | 8/1966 | Velter | ...................... A47F 1/085 |
| | | | | | 221/242 |
| 3,592,355 | A | * | 7/1971 | Manzer | ................... G07F 13/10 |
| | | | | | 221/104 |
| 4,260,581 | A | | 4/1981 | Sakurada | |
| 4,804,108 | A | * | 2/1989 | Ficken | ................. B65G 59/102 |
| | | | | | 221/223 |
| 5,024,048 | A | * | 6/1991 | Moore | .................... B65B 43/44 |
| | | | | | 221/221 |

(Continued)

FOREIGN PATENT DOCUMENTS

EP 0 710 840 5/1996
EP 0806672 11/1997

(Continued)

Primary Examiner — Rakesh Kumar
(74) Attorney, Agent, or Firm — 24IP Law Group; Timothy R DeWitt (57) ABSTRACT Device for storing and dispensing cuvettes from a stack. The device has at least one cuvette stack receiving compartment, which may be a tube open at both ends, wherein one of the openings is provided with retaining springs, partly blocking the opening, so that the cuvette stack having been dropped into the compartment may come to rest on the retaining springs. The retaining springs are being spaced apart from the opening of the compartment by a distance that allows at least two cuvettes in the stack to stick out of the compartment opening. Furthermore, a cuvette separator with retaining spring spreaders is provided, moveable between a standby position away from the compartment and a cuvette separation position across the retaining spring opening of the compartment, and in between the two cuvettes, sticking out of the compartment.

11 Claims, 7 Drawing Sheets

(56) References Cited

U.S. PATENT DOCUMENTS

| | | | | |
|---|---|---|---|---|
| 6,881,380 | B1* | 4/2005 | Mootz | B65G 59/062 221/298 |
| 7,731,058 | B2* | 6/2010 | Stamatis Filho | A47F 1/10 194/247 |
| 7,731,899 | B2* | 6/2010 | Talmer et al. | 422/64 |
| 8,016,158 | B2* | 9/2011 | Walsh | A47F 1/106 221/223 |
| 8,418,880 | B2* | 4/2013 | Yu | G01J 5/021 206/438 |
| 8,480,954 | B2* | 7/2013 | Talmer | G01N 35/025 422/63 |
| 9,017,008 | B2* | 4/2015 | Beressey | B65G 59/105 414/796.9 |
| 2006/0169712 | A1* | 8/2006 | Yitzchaki | G07F 13/10 221/221 |
| 2007/0253866 | A1* | 11/2007 | Rousseau | B01L 3/50855 422/64 |
| 2007/0278240 | A1* | 12/2007 | Dideriksen | B65G 59/108 221/1 |
| 2008/0193332 | A1* | 8/2008 | Talmer | G01N 35/025 422/63 |
| 2011/0299568 | A1* | 12/2011 | Huang | A47F 1/10 374/209 |
| 2014/0319163 | A1* | 10/2014 | Lukhaub | G01N 35/04 221/1 |

FOREIGN PATENT DOCUMENTS

| | | |
|---|---|---|
| WO | 9611866 | 4/1996 |
| WO | 2008097892 | 8/2008 |

* cited by examiner

CUVETTE HANDLING DEVICE

BACKGROUND OF THE INVENTION

1. Field of the Invention

The present invention is directed to a device, use of the device in medical analysis systems, and a method for handling cuvettes for use in medical analysis systems, as described by the independent patent claims.

2. Brief Description of the Related Art

In medical analysis systems disposable cuvettes are used. These are loaded into a system by the user, and are handed over by a cuvette handling module to the next module one by one.

Currently cuvettes are packed in bags as bulk ware. Hardware to sort and align the cuvettes is needed to make them usable in medical analysis systems. In existing systems conveyor pots and screw conveyors are used to transfer the cuvettes loaded by the user into the handling system of a medical analysis system. However, the sorting and alignment hardware for bulk cuvettes is more complex. It is expensive and may cause reliability issues, while requiring a lot of space in the system, which in turn is ineffective and costly.

Some devices for transferring somewhat arranged cuvettes are also known.

For example, WO 2008/097892 discloses stackable cuvettes and a cuvette dispenser. Release members rotate to release cuvettes from cuvette stacks. US 2007/0253866 discloses cuvettes which can be arranged in plates, not in stacks, and an analytical device using these cuvettes. EP 0 806 672 A3 teaches multiple vertically oriented cuvettes and a device for releasing the bottom cuvette. And WO 96/11866 discloses a vertical row of cuvettes and a device for releasing the bottom cuvette. Once released, the bottom cuvette changes orientation.

There is a need for improved devices and methods for handling cuvettes for use in medical analysis systems, as well as improved cuvettes as such that are reliable, effective and easy to use.

SUMMARY OF THE INVENTION

This object is solved by the handling devices for cuvettes, as well as the method for handling cuvettes according to the independent claims, while the features of the dependant claims describe preferred embodiments.

What is provided is a device for storing and dispensing cuvettes from a stack. The device has at least one cuvette stack receiving compartment, which may be a tube open at both ends, wherein one of the openings is provided with retaining devices, such as for example springs, partly blocking the opening, so that the cuvette stack having been dropped into the compartment may come to rest on the retaining springs. The retaining springs are being spaced apart from the opening of the compartment by a distance that allows at least two cuvettes in the stack to stick out of the compartment opening. Furthermore, a cuvette separator with retaining spring spreaders is provided, moveable between a standby position away from the compartment and a cuvette separation position across the retaining spring opening of the compartment, and in between the two cuvettes, sticking out of the compartment. By moving the cuvette separator in between the cuvettes, the retaining spring spreaders of the cuvette separator elastically deflects the retaining springs aside so that the lowest of the cuvettes in the stack received in the compartment can be separate from the stack.

In a preferred embodiment the cuvette separator is moveable perpendicularly with respect to extension of the tube of the cuvette stack receiving compartment. Furthermore, the cuvette separator may consist of two parallel double T profiles disposed at a distance corresponding approximately to the width of the cuvette, wherein at least two parallel profile flanks are provided with ramps for separating two adjacent cuvettes in a cuvette stack by pushing the stacking flanges of the cuvettes apart, and unclipping the clipping elements, when the separator is moved across the retaining spring opening of the compartment, and in between two cuvettes in the stack contained in the compartment.

The device might store and dispense cuvettes which are disposable cuvettes for use in medical analysis systems, which have a stackable shape and are provided with clipping elements for releasable clipping cuvettes in a stack to one another. This creates a stable stack with no additional packing material needed. Furthermore, the clipped cuvettes may be delivered stacked. The stacks are simply packed in a plastic bag before being put into the transport box and delivered to the customer. The stacks can then be taken out of the box and put into a loading funnel of a cuvette handling module.

In a preferred embodiment, the cuvette is provided with a sample receiving part and a handling flange containing the clipping elements, wherein the clipping elements preferably are integrally formed into the cuvette, and the clipping elements may be formed as clipping tongues and clipping openings, wherein the respective clipping opening is located at the foot of the respective clipping tongue.

Use of the device in medical analysis systems is also provided.

Furthermore, a method for storing and dispensing clipped cuvettes from a stack is disclosed, comprising the steps of loading a stack of clipped cuvettes into a compartment tube open at both ends by means of a loading funnel, dropping the stack of clipped cuvettes onto retaining springs at one end of the compartment, and moving a cuvette separator with retaining spring spreaders from a standby position into a cuvette separation position across the retaining spring opening of the compartment and in between the two cuvettes sticking out of the compartment.

The cuvettes might have further features, as described above.

All of the measures above have the following advantages in contrast to systems and methods as known from the prior art. Handling of stacked cuvettes is much easier. The mechanical hardware needed is less complicated and the design is more compact, so that less room is needed in the system. Cuvettes need less space during transport and in the system, due to stacking them in an orderly manner. At the same time, cuvettes are protected against damage during transport and use, and they stay clean, as they do not fall around in bulk bags. Furthermore, due to the fact that cuvettes are stacked and clipped together, it is easier to estimate the number of cuvettes being placed in the system at a time.

BRIEF DESCRIPTION OF THE DRAWINGS

Further details and advantages of the present invention can be taken from the following, non limiting, description of a preferred embodiment under reference to the figures enclosed herewith, wherein identical elements have identical reference signs, the figures showing:

FIG. 6 a-h schematic cross sectional views of the cuvette separation process and the means for performing it;

DETAILED DESCRIPTION OF THE PREFERRED EMBODIMENTS

Figure 1:
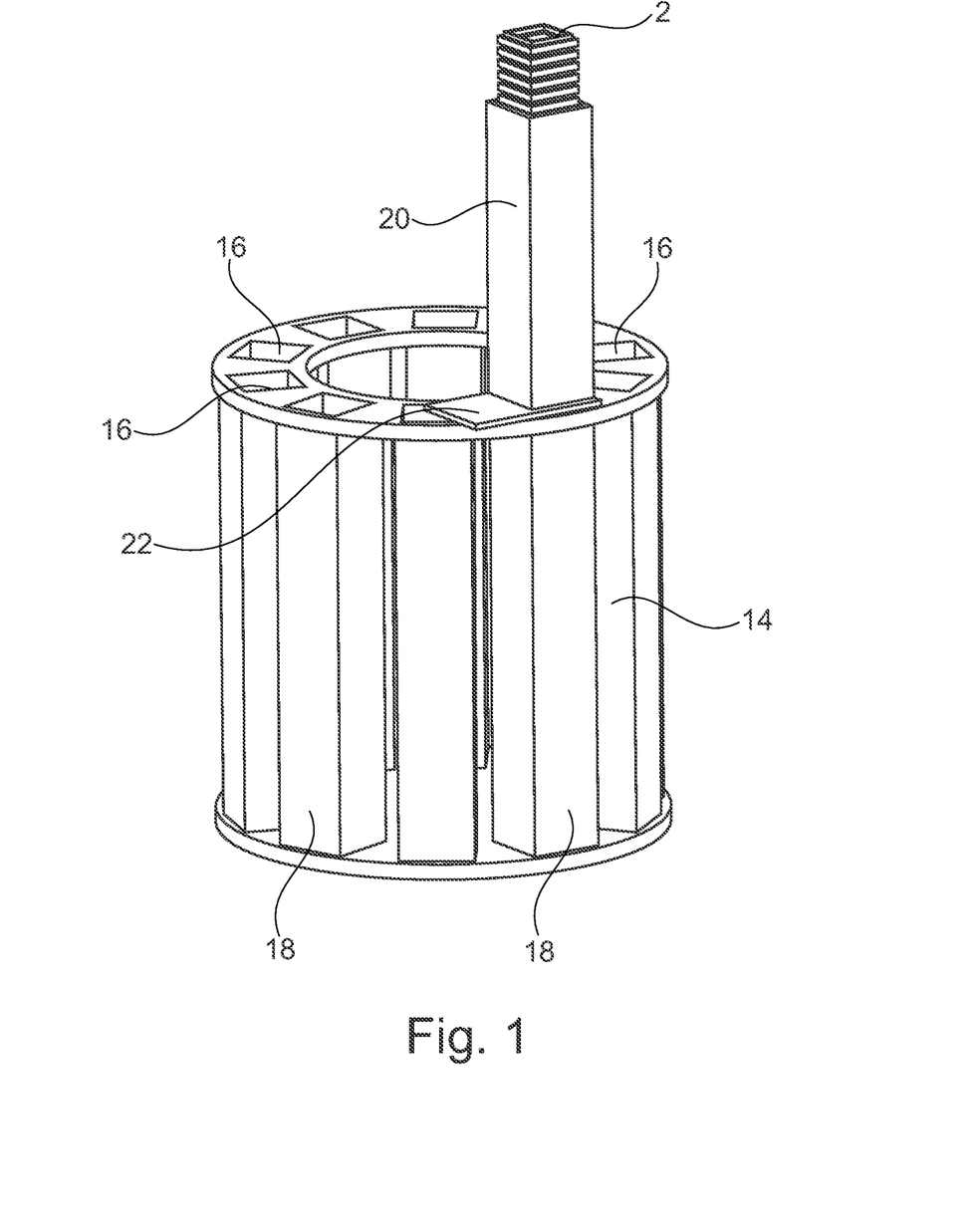
FIG. 1 a perspective view of a cuvette carousel with compartments for cuvettes in stacks.

FIG. 1 shows a perspective view of a cuvette carousel 14, with a multitude of cuvette receiving compartments 16 that are being formed by rectangular tubes 18. As shown in FIG. 1, a loading funnel 20 is provided in which a stack of cuvettes 2 is preloaded. In FIG. 1, the lower end opening of the loading funnel is still closed by a compartment lid 22.

Figure 2:
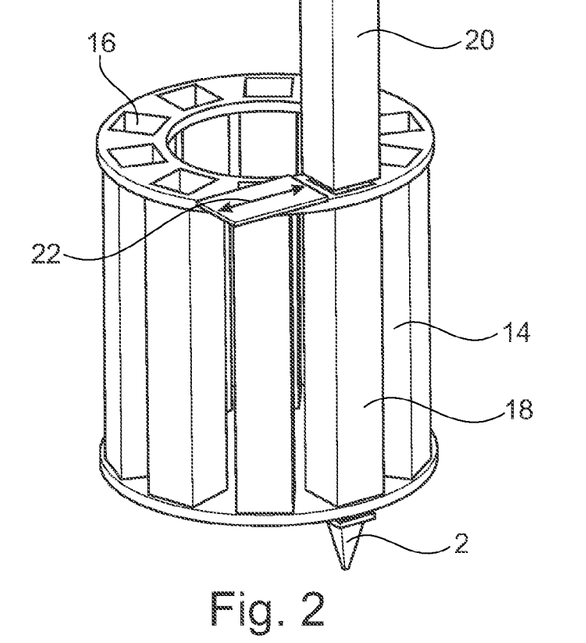
FIG. 2 a perspective view of the carousel according to FIG. 1 with a stack of cuvettes within a stack receiving compartment.

FIG. 2 shows the same carousel 14 as in FIG. 1. However, the compartment lid 22 in this FIG. 2 was opened, and the stack of cuvettes dropped into the compartment 16 being formed by the rectangular tubes 18. The stack of cuvettes 2 drops into the compartment 16, until it reaches the separation position where it is stopped by two retaining springs, which will be described later on. In this position, the last and second to last cuvettes 2 are visible and accessible below the cuvette carousel 14, as can be seen in FIG. 2.

Figure 3:
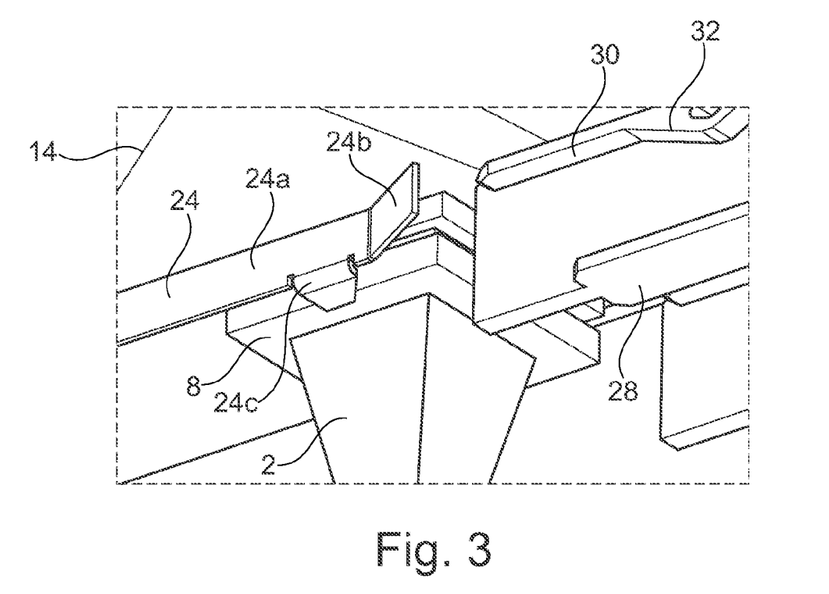
FIG. 3 a partial detail view of the lower end of the compartment in the carousel according to FIGS. 1 and 2, and a cuvette separator to release the lowest of cuvettes in the stack.

As can be taken from FIG. 3, which is a partial perspective view of the underside of the carousel 14, the lowermost cuvette 2 rests on two retaining springs 24 (only one shown). Those retaining springs 24 are made in the form of elastic tongues 24a, with deflection ramps 24b at the end, as well as the actual retaining projections 24c on which the cuvette comes to rest with the handling flange 8. What can be taken from FIG. 3 as well, is that a separator 28 is provided, which can be moved across the opening of the compartment 16 of the carousel 14 and in between the handling flanges 8 of the lowermost two cuvettes 2. When the separator 28 is moved towards the center of the carousel and in between the cuvettes 2, the upper flanks 30 of the separator 28 interacts with the deflection ramps 24b of the retaining springs and moves the latter outward, so that the second to last cuvette does not rest on the retaining projection 24c anymore, but on the upper flanks 30 of the double t profile forming the separator 28. The lowermost cuvette will be separated from the stack by separation ramps 32, unclipping the clipping elements 6 between the lowermost and the second but last cuvette 2. The unclipped cuvette drops to the lower fin. After a reverse movement of the separator, the cuvette drops off the lower fin and unclipping is finished.

Figure 4:
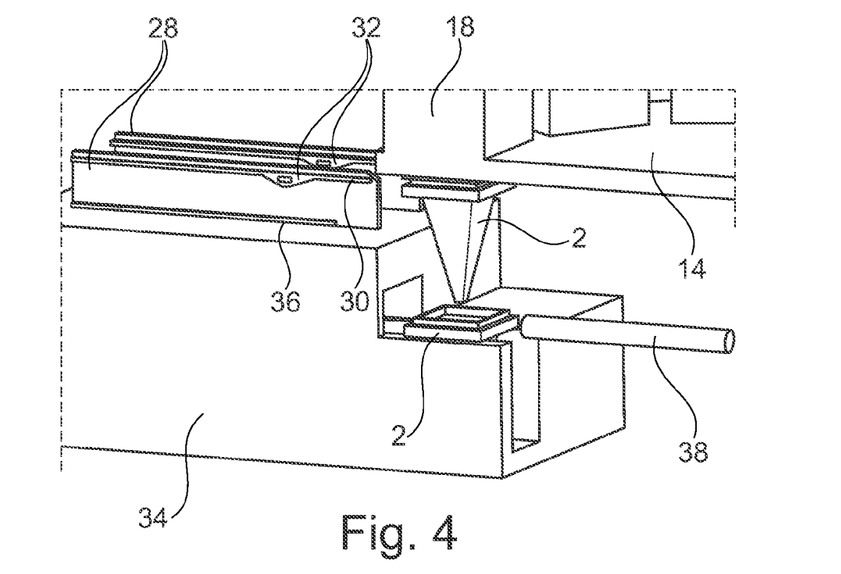
FIG. 4 a partial, cross sectional view of the carousel according to FIG. 1, the cuvette separator and a module to be loaded with cuvettes.

FIG. 4 shows a different perspective view of the situation as shown in FIG. 3 already, with the difference that the lowermost cuvette 2 was separated from the stack in the compartment 16 or tube 18 in the carousel 14 already, and with the difference that no retaining springs 24 are shown. Beyond the features already known from FIG. 3, FIG. 4 also shows a module 34 to be loaded with a cuvette 2 and pusher 38 to push the cuvette 2 which was separated from the stack into the module 34. Furthermore, more details of the separator 28 are shown, in particular lower flanks 36 of the double t profiles, being arranged in parallel and forming the separator. As can be seen, the lower flanks 36 of the separator 28 are shorter than the upper flanks 30, which extend all the way to the end of the respective profile, while to the lower flanks 36 terminate way before the end of the profile, to make sure that the cuvette can drop off during the reverse movement.

Figure 5:
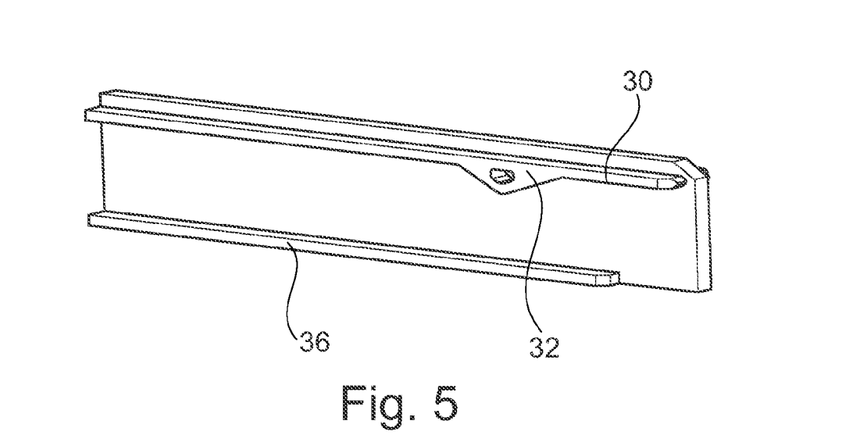
FIG. 5 a perspective view of one of the two double t profiles of the separator according to FIG. 2.

An even better view of one of the double t profiles forming the separator 28 can be seen in FIG. 5. In particular, it may be noted that the outer ends of the upper flanks 30 are chamfered in order to be able to deflect the retaining springs, as can be taken from FIG. 3.

Figure 6:
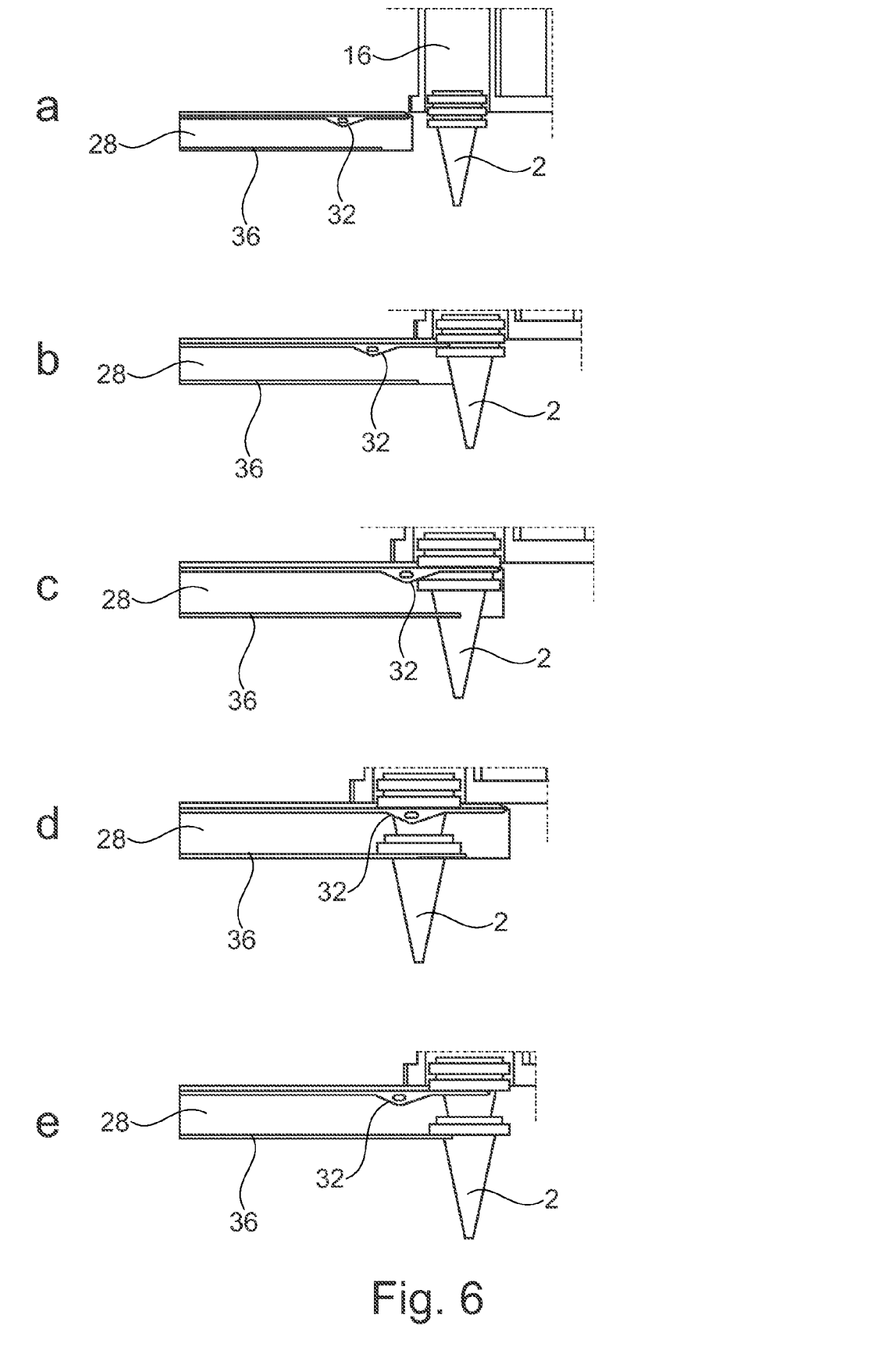

Finally, FIG. 6 shows the different stages of the process of separating a cuvette 2 from the stack. Single steps are depicted in FIG. 6 a to h as follows:

FIG. 6a: Cuvettes 2 are ready for separation. Separator 28 is in park position away from the stacks of cuvettes 2. Retaining springs 24 (not shown on these pictures) are holding the cuvettes 2 within the compartment 16.

FIG. 6b: Separator 28 moves towards centre of carousel 14. The upper flank 30 enters the gap between the last and next to last cuvette 2. Retaining springs 24 (not shown here) are being pushed to the side so the stack of cuvettes 2 rests completely on the upper flank 30 of the separator 28.

FIG. 6c: Separation ramp 32 pushes the last cuvette 2 down until it unclips.

FIG. 6d: The last cuvette 2 unclips and drops to the lower flanks 36 of the separator 28.

FIG. 6e: The separator 28 reverses direction.

FIG. 6f: Lower flank 36 ends. The separated cuvette 2 drops on push over platform of the module 34. Retaining springs 24 (not shown here) closes again.

FIG. 6g: The separator 28 returns to park position. The upper flank 30 ends. The cuvette 2 stack drops on the closed retaining springs 24 (not shown here). Separated cuvette 2 ready to be loaded.

FIG. 6h: The pusher 38 pushes the separated cuvette 2 into module 34.

Figure 7:
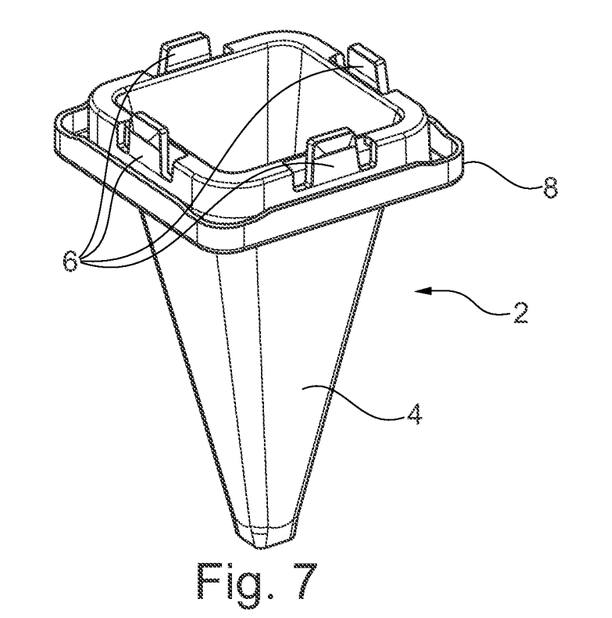
FIG. 7 a perspective view of a disposable cuvette according to the present invention.

FIG. 7 shows a perspective view of a disposable cuvette 2 for use in medical systems according to the present invention. As can be taken from FIG. 7 the cuvette 2 has a stackable, conical shape of the sample receiving part 4 and is provided with clipping elements 6 for releasable clipping cuvettes 2 in a stack to one another, the clipping elements being located on a handling flange 8, which, when the cuvettes are stacked into one another, forms an outer shape of the entire stack which allows it to be packed into a tray without any problems.

Figure 8:
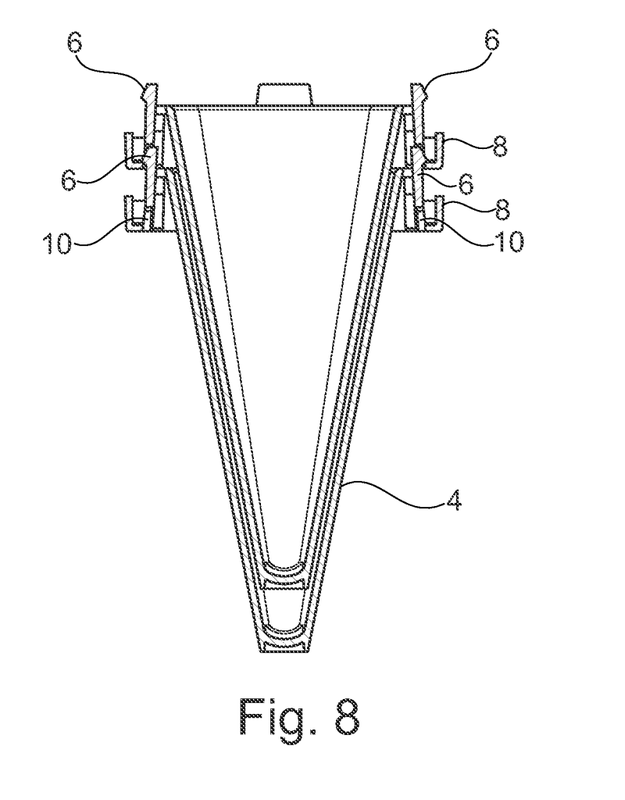
FIG. 8 a cross section through to cuvettes according to FIG. 7, stacked and clipped into each other.

FIG. 8 shows a cross sectional view of the cuvette 2 according to FIG. 7. What can be taken in more detail in FIG. 8 is the conical, stackable shape of the sample receiving part of the cuvette 4, as well as the handling flange 8, forming a straight outer shape of the stacked cuvettes. As can be taken from FIG. 8 as well is the fact that the clipping elements 6 are integrally formed into the cuvette 2 at the upper rim. In fact, in the embodiment shown in FIG. 8, the clipping elements 6 are formed as clipping tongues and clipping openings 10, wherein the respective clipping opening is located at the foot of the respective clipping tongue.

Figure 9:
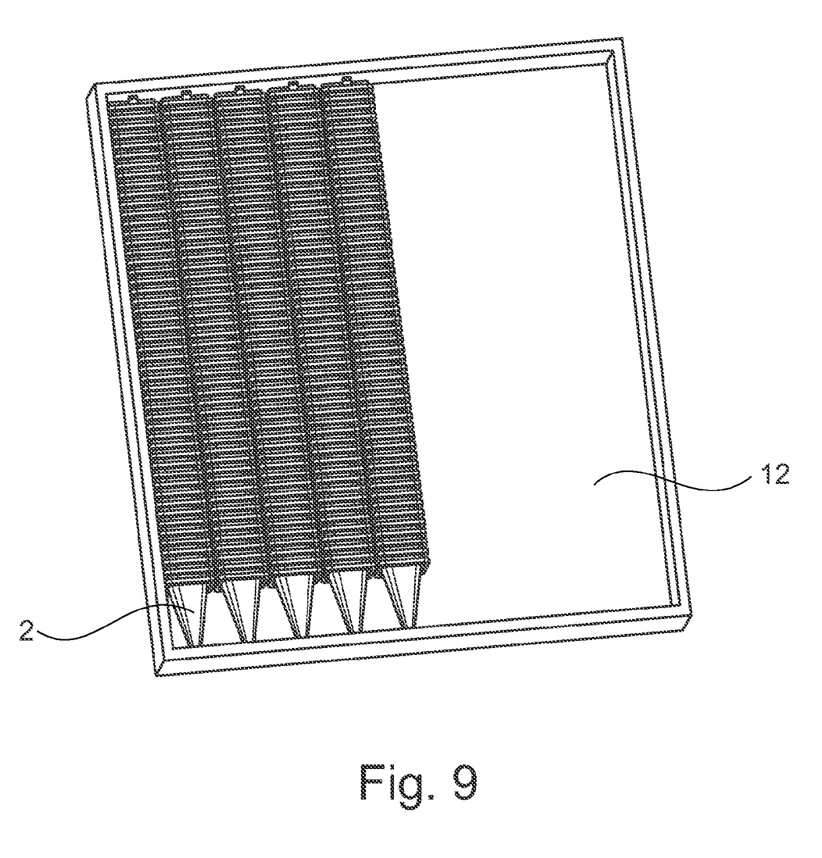
FIG. 9 a perspective view of stacks of cuvettes according to FIGS. 7 and 8 in a transport box.

FIG. 9 shows a perspective view of stacks of cuvettes according to FIGS. 7 and 8 being placed in a transport box 12. What can easily be taken from this figure is the efficient outer shape of the cuvette stacks that are a result of the handling flanges 8.

What is claimed is:

1. A device for storing and dispensing cuvettes from a stack, wherein at least one cuvette stack receiving compartment is provided, characterized in that
   a. the compartment is a tube comprising openings at both ends, wherein one of the openings is provided with retaining springs, partly blocking the opening;
   b. the retaining springs are being spaced apart from the opening of the compartment in order to allow at least two cuvettes in the stack to stick out;
   c. a cuvette separator with retaining spring spreaders is provided, moveable between a standby position away from the compartment and a cuvette separation position across the retaining spring opening of the compartment, and in between the two cuvettes, sticking out of the compartment, wherein the cuvette separator consists of two parallel double T profiles disposed at a distance corresponding approximately to the width of the cuvette, wherein at least two parallel profile flanks are provided with ramps for separating two adjacent cuvettes in a cuvette stack, when the separator is moved across the retaining spring opening of the compartment, and in between two cuvettes in the stack contained in the compartment.

2. A device according to claim 1, wherein the cuvette separator is moveable perpendicularly with respect to extension of the tube of the cuvette stack receiving compartment.

3. Use of the device according to claim 1 in medical analysis systems.

4. A device according to claim 1, wherein the cuvette is a disposable cuvette for use in medical analysis systems, characterized in that the cuvette has a stackable shape and is provided with clipping elements for releasable clipping cuvettes in a stack to one another.

5. A device according to claim 4, wherein the cuvette is provided with a sample receiving part and a handling flange containing the clipping elements.

6. A device according to claim 4, wherein the clipping elements are integrally formed into the cuvette.

7. A device according to claim 4, wherein the clipping elements are formed as clipping tongues and clipping openings, wherein the respective clipping opening is located at the foot of the respective clipping tongue.

8. A method for storing and dispensing cuvettes from a stack, wherein the cuvette is a disposable cuvette for use in medical analysis systems, characterized in that the cuvette has a stackable shape and is provided with clipping elements for releasable clipping cuvettes in a stack to one another comprising the steps of:
   a. loading a stack of clipped cuvettes into a compartment tube open at both ends,
   b. dropping the stack of clipped cuvettes onto retaining springs at one end of the compartment tube,
   c. moving a cuvette separator having two parallel double T profiles disposed at a distance corresponding approximately to the width of the cuvette and at least two parallel profile flanks with ramps for separating two adjacent cuvettes in a cuvette stack from a standby position into a cuvette separation position across the retaining springs opening of the compartment tube and in between two cuvettes sticking out of the compartment.

9. A method according to claim 8, wherein the clipping elements are formed as clipping tongues and clipping openings, wherein the respective clipping opening is located at the foot of the respective clipping tongue.

10. A method according to claim 8, wherein the cuvette is provided with a sample receiving part and a handling flange containing the clipping elements.

11. A method according to claim 8, wherein the clipping elements are integrally formed into the cuvette.

* * * * *